United States Patent
Letant et al.

(10) Patent No.: US 7,155,076 B2
(45) Date of Patent: Dec. 26, 2006

(54) TARGET MOLECULES DETECTION BY WAVEGUIDING IN A PHOTONIC SILICON MEMBRANE

(75) Inventors: Sonia E. Letant, Livermore, CA (US); Anthony Van Buuren, Livermore, CA (US); Louis Terminello, Danville, CA (US); Bradley R. Hart, Brentwood, CA (US)

(73) Assignee: The Regents of the University of California, Oakland, CA (US)

( * ) Notice: Subject to any disclaimer, the term of this patent is extended or adjusted under 35 U.S.C. 154(b) by 94 days.

(21) Appl. No.: 10/833,573

(22) Filed: Apr. 27, 2004

(65) Prior Publication Data

US 2004/0228568 A1 Nov. 18, 2004

Related U.S. Application Data

(63) Continuation-in-part of application No. 10/159,175, filed on May 31, 2002, now Pat. No. 6,785,432.

(51) Int. Cl.
*G02B 6/00* (2006.01)
*G02B 6/10* (2006.01)

(52) U.S. Cl. .......................... 385/12; 385/14; 385/129; 385/130

(58) Field of Classification Search .................. 385/12, 385/14, 129, 130; 250/227.11, 227.14; 422/82.05, 422/82.06, 82.08, 82.09, 82.11
See application file for complete search history.

(56) References Cited

U.S. PATENT DOCUMENTS

| | | | | |
|---|---|---|---|---|
| 5,485,277 A | * | 1/1996 | Foster | 356/445 |
| 5,496,701 A | * | 3/1996 | Pollard-Knight | 435/7.4 |
| 5,832,165 A | * | 11/1998 | Reichert et al. | 385/130 |
| 5,843,767 A | * | 12/1998 | Beattie | 435/287.1 |
| 6,023,540 A | * | 2/2000 | Walt et al. | 385/12 |
| 6,356,676 B1 | * | 3/2002 | Herron et al. | 385/12 |
| 6,611,634 B1 | * | 8/2003 | Herron et al. | 385/12 |
| 6,785,432 B1 | * | 8/2004 | Letant et al. | 385/12 |
| 6,801,677 B1 | * | 10/2004 | Grace et al. | 385/12 |
| 6,829,073 B1 | * | 12/2004 | Krol et al. | 359/263 |
| 2004/0023396 A1 | * | 2/2004 | Boyd et al. | 435/872 |
| 2005/0078903 A1 | * | 4/2005 | Grace et al. | 385/12 |
| 2005/0135723 A1 | * | 6/2005 | Carr et al. | 385/12 |

* cited by examiner

*Primary Examiner*—Kevin S. Wood
(74) *Attorney, Agent, or Firm*—Eddie E. Scott; Ann M. Lee

(57) ABSTRACT

Disclosed herein is a porous silicon filter capable of binding and detecting biological and chemical target molecules in liquid or gas samples. A photonic waveguiding silicon filter with chemical and/or biological anchors covalently attached to the pore walls bind target molecules. The system uses transmission curve engineering principles to allow measurements to be made in situ and in real time to detect the presence of various target molecules and calculate the concentration of bound target.

3 Claims, 13 Drawing Sheets

10 μm

30 μm

30 μm

TARGET MOLECULES DETECTION BY WAVEGUIDING IN A PHOTONIC SILICON MEMBRANE

This application is a Continuation in Part of U.S. application Ser. No. 10/159,175 filed May 31, 2002 titled "Target Molecules Detection by Waveguiding in a Photonic Silicon Membrane," now U.S. Pat. No. 6,785,432, issued Aug. 31, 2004.

The United States Government has rights in this invention pursuant to Contract No. W-7405-ENG-48 between the United States Department of Energy and the University of California for the operation of Lawrence Livermore National Laboratory.

BACKGROUND OF THE INVENTION

Extensive work has been performed during the last ten years to build and investigate photonic crystals, the optical analogues to electronic semiconductors. Photonic crystals are materials built to present a periodic variation of refractive index. The periodicity being the same order of magnitude as the wavelength of the electromagnetic (EM) waves, these structures exhibit band gaps for photons. The propagation of the EM waves can be controlled by changing the periodicity and introducing point or line defects in the photonic crystal. A. Birner et al in, "Silicon-based photonic crystals," *Adv. Mater.* 13, 377–388 (2001), recently reviewed 1D, 2D, and 3D photonic crystals made out of silicon.

Foresi et al in, "Photonic-bandgap microcavities in optical waveguides," *Nature* 390, 143–145 (1997) disclose that 1D structures and Birner et al in, "Transmission of microcavity structure in a two-dimentional photonic crystal based on macroporous silicon," *Materials Science in Semiconductor Processing* 3, 487–491 (2000), disclose that 2D structures are usually built by drilling well-controlled pores in a silicon wafer by electrochemical etch or by electron beam lithography. In, "Large-scale synthesis of a silicon photonic crystal with a complete three-dimensional bandgap near 1.4 micrometer," *Nature* 405, 437–440 (2000), Blanco et al disclose that 3D structures usually involve the growth of a crystal by chemical vacuum deposition on a periodic template followed by the dissolution of the template (inverse opal structure).

SUMMARY OF THE INVENTION

An aspect of the invention includes a photonic waveguiding device comprising: at least one silicon wafer having a plurality of through pores distributed according to a designed pattern leading to a photonic band gap; and at least one chemical or biological target specific anchor attached to the inner wall of at least one of the pores, wherein the anchor is capable of binding to a specific chemical or biological target molecule.

Another aspect of the invention includes a photonic waveguiding device comprising: an array of waveguiding filters, wherein each filter is functionalized with a chemical or biological target specific anchor to allow the contemporaneous detection of various chemical and biological target molecules and wherein each of the filters comprise (1) a silicon wafer having a plurality of through pores distributed according to a designed pattern leading to a photonic band gap and (2) a chemical or biological target specific anchor attached to the inner wall of at least one of the pores, the anchor being capable of binding to a chemical or biological target molecule.

A further aspect of the invention includes a photonic waveguiding detection system comprising: a light source; at least one silicon waveguiding filter, wherein the filter comprises a silicon wafer having (1) a plurality of through pores distributed according to a designed pattern leading to a photonic band gap and (2) at least one chemical or biological target specific anchor attached to the inner wall of at least one of the pores, wherein the anchor is capable of binding to a chemical or biological target molecule; a detector to count the photons transmitted through the device; and a computer to analyze the light transmitted through the filter by (1) recording the intensity and wavelength of light transmitted through the filter, (2) identifying the presence of target molecules bound in the device and (3) determining the concentration of bound target molecules.

A further aspect of the invention includes a method comprising: measuring the transmission curve through at least one silicon filtering device, wherein the filtering device comprises (1) a plurality of through pores distributed according to a designed pattern leading to a photonic band gap and (2) at least one chemical or biological target specific anchor attached to the inner wall of at least one of the pores, wherein the anchor is capable of binding to a chemical or biological target molecule; passing a sample through the silicon filter, the sample being a gas or a liquid; shining a light orthogonal to the pores of the silicon filter, while contemporaneously flowing the sample through the filter; and measuring the transmission curve of the waveguiding silicon filter as the sample passes through the filter, wherein modifications in the transmission curve are (1) indicative that at least one of the target molecules has bound to the anchor and (2) indicative of the concentration of the bound target molecules.

Another aspect of the invention includes a method comprising: fabricating a silicon membrane with an array of pores designed for opening a photonic band gap and for waveguiding; functionalizing the pore walls of the silicon membrane with chemical functional groups; and attaching biological or chemical anchors to the functionalized walls of the membrane to create a silicon photonic waveguiding filter.

DETAILED DESCRIPTION

Theory

Figure 1A:
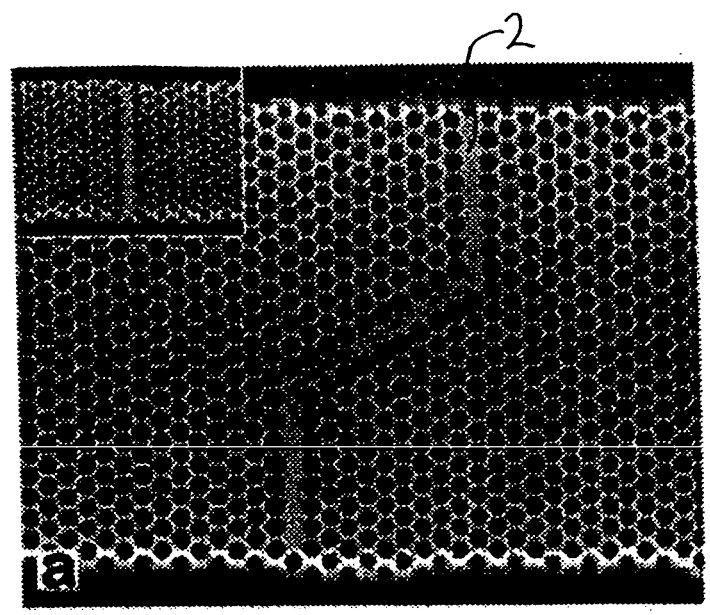
FIG. 1a is a top view SEM picture showing line defects embedded in 2D photonic silicon crystals.
Figure 1B:
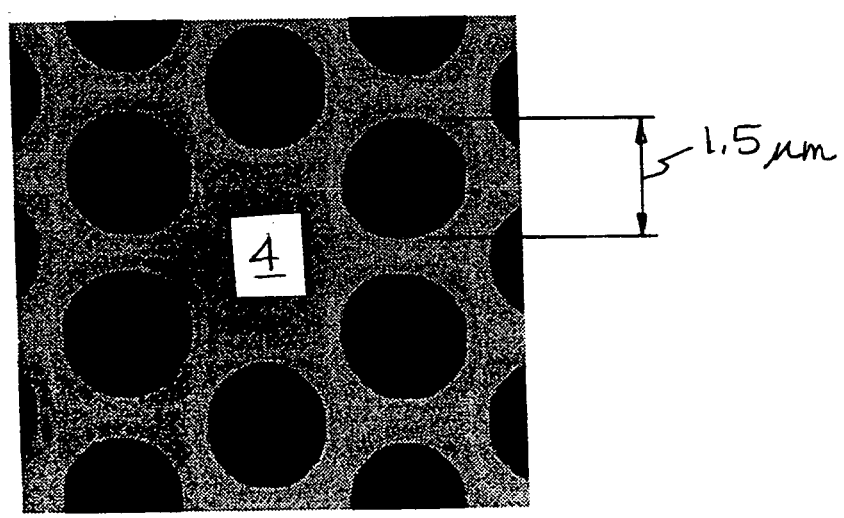
FIG. 1b is a top view SEM picture showing point defects embedded in 2D photonic silicon crystals.

Canham discloses in, "Quantum Wire Array Fabrication by Electrochemical and Chemical Dissolution," *Appl. Phys. Lett* 57, 1046–1048 (1990), that randomly positioned pores can be created in silicon by electrochemical etch in an aqueous solution of hydrofluoric acid (HF), water and ethanol. Electrochemical parameters such as the current density, the HF concentration and the duration of the etch and physical parameters such as the doping type and level of the silicon substrate determine the diameter, length and density of the pores formed. Lehmann et al in, "Formation mechanism and properties of electrochemically etched trenches in n-type silicon," *J. Electrochem. Soc.* 137, 653–659 (1990), have shown that it is possible to pre-determine the location of the pores by patterning n-type silicon substrates with inverted pyramids (nucleation pits). These pits are made by standard lithography followed by potassium hydroxide (KOH) etch. The pores are then grown on the nucleation pits by applying back-side illumination during the HF electrochemical etch. The resulting material presents parallel pores, distributed according to the designed pattern. Any kind of pore pattern can potentially be achieved. Birner et al. in "Silicon-based photonic crystal," *Adv. Mater.* 13, 377–388 (2001), disclose SEM top views of line and point defects embedded in 2D photonic silicon crystals, prepared by the electrochemical etching technique. The introduction of defects disturbs the translational symmetry of the periodic lattice and can lead to the formation of localized states (modes) in the band gap. FIGS. 1a and 1b are taken from the Birner et al disclosure. FIG. 1a demonstrates that line defects 2 and FIG. 1b demonstrates that point defects 4 can also be introduced in the pattern in order to engineer the transmission curve of the photonic crystal. Pore diameters can be tuned from about 1 micron to about 500 nanometers. A decrease of pore diameter to about 100 mn or less allows the opening of photonic band gaps in the visible range.

Figure 2:
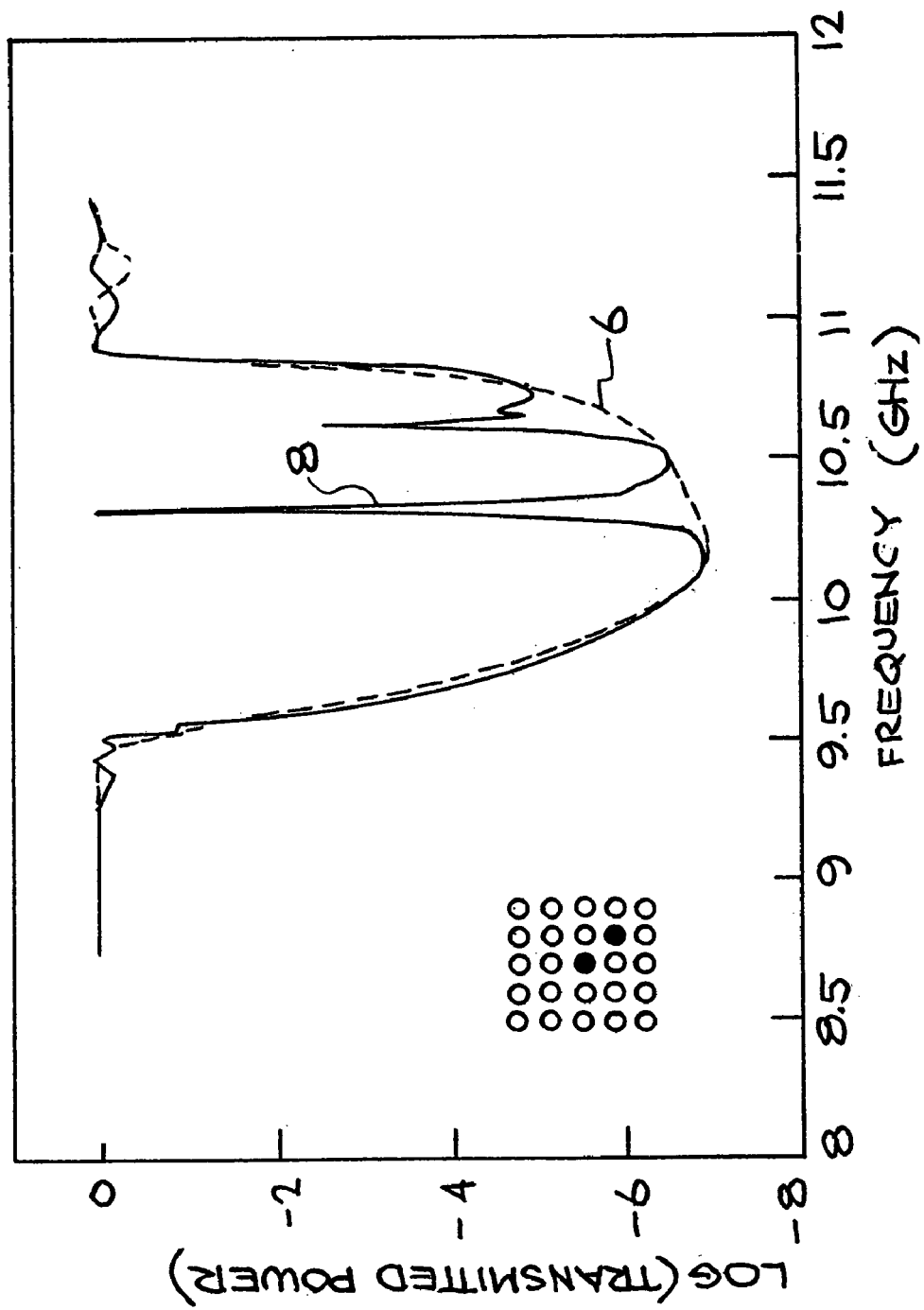
FIG. 2 is a graph of a calculated transmission curve for a perfect 2D photonic crystal and for the same crystal with two point defects.

In "Photonic band gaps and defects in two dimensions: studies of the transmission coefficient," *Phys. Rev. B* 48, 14121–14126 (1993), Sigalas et al. present the theory of propagation of EM waves in 2D photonic crystals made of dielectric rods separated by voids. This group investigated the case where EM waves propagate in a plane perpendicular to the axes of the cylinders for perfect crystals and for crystals with point defects. Experiments conducted by McCall et al. in "Microwave propagation in two-dimensional dielectric lattices," *Phys. Rev. Lett.* 67, 2017–2020 (1991), showed that the transmission curve of a perfect 2D photonic crystal presents band gaps and that the position of these band gaps depend on the periodicity, geometry and dielectric constant of the materials used. FIG. 2, taken from Sigalas et al, shows calculated transmission curves 6 and 8 (EM waves propagate in a plane perpendicular to the axes of the cylinders) for a perfect 2D photonic crystal 6 (dotted line) and for the same crystal with two point defects 8 (solid line). The two defects appear as two sharp modes in the phototonic band gap. FIG. 2 illustrates the effect of the introduction of point defects in a photonic crystal, which is to create localized states in the band gap.

The design of smart membranes through chemical functionalization of semi-conductor substrates with well-defined pore structures is described herein. A versatile class of new materials can be designed by attaching chemically or biologically specific anchors onto semi-conductor devices. Utilizing the well-defined pore morphology of silicon enhances the collection of targets and lowers the detection level. Novel membranes with the ability to selectively recognize and bind target molecules, such as proteins, DNA fragments, enzymes and other biologically relevant macromolecules, can be prepared by controlling both the pore morphology and the chemical affinity of the membrane surface.

Figure 3B:
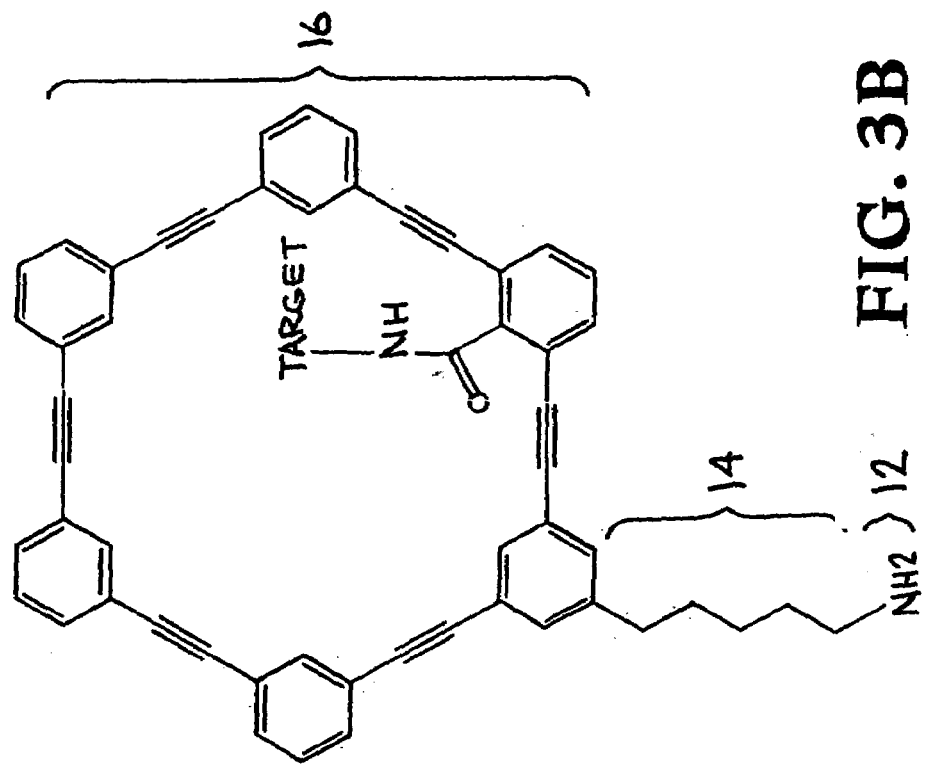
FIG. 3b shows the chemical structure of an amine functionalized macro-cycle.
Figure 3A:
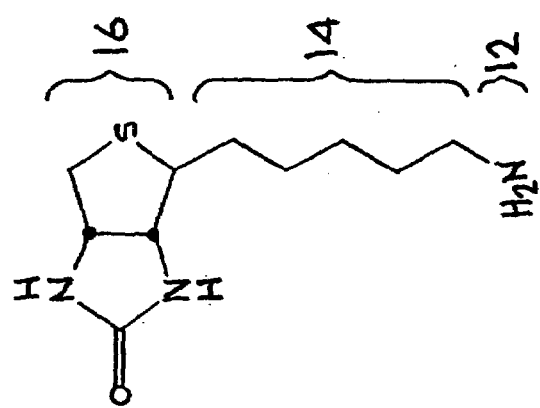
FIG. 3a shows the chemical structure of an amine functionalized biotin.
Figure 3C:
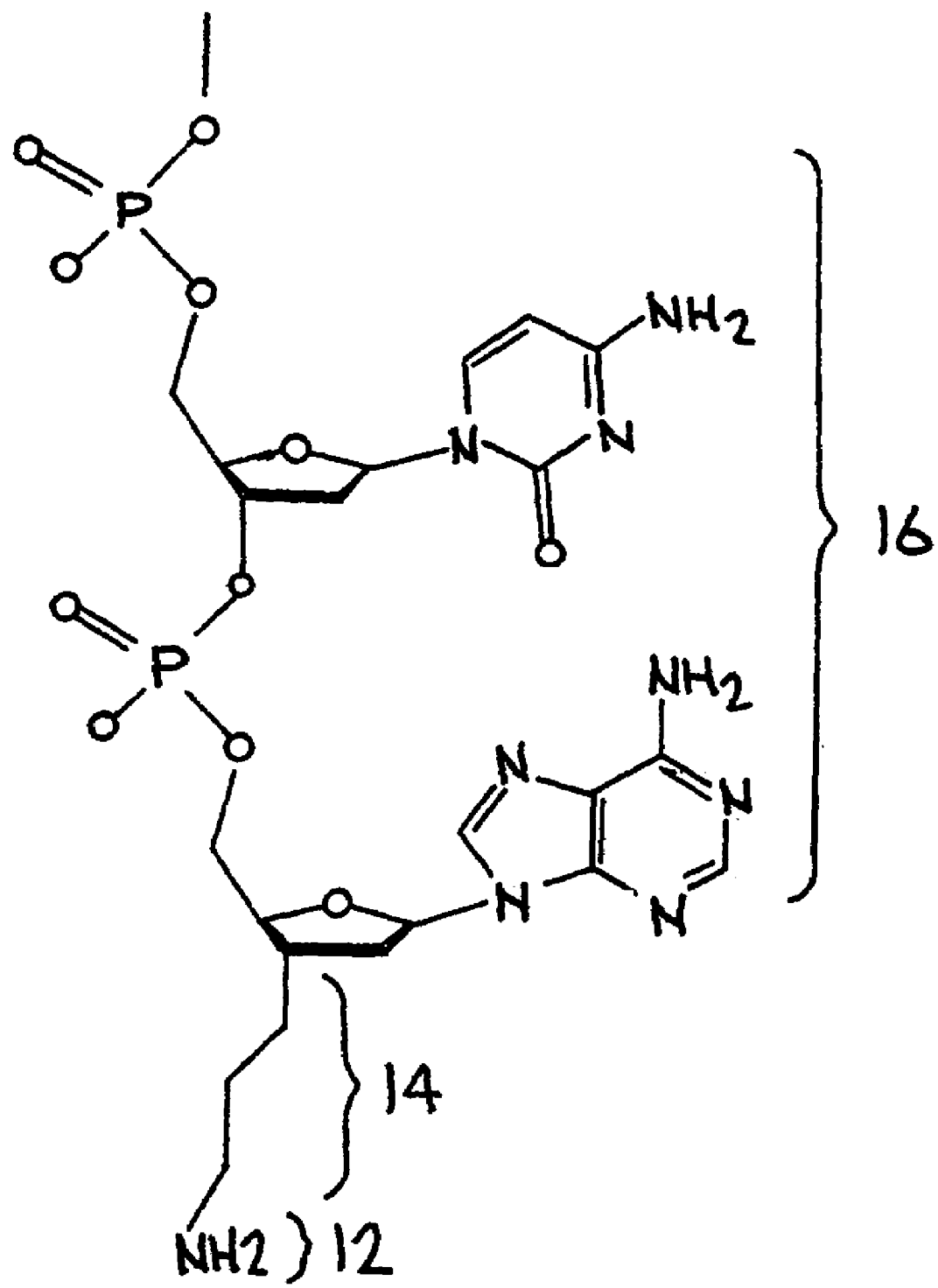
FIG. 3c shows the chemical structure of an amine functionalized single DNA strand.
Figure 4A:
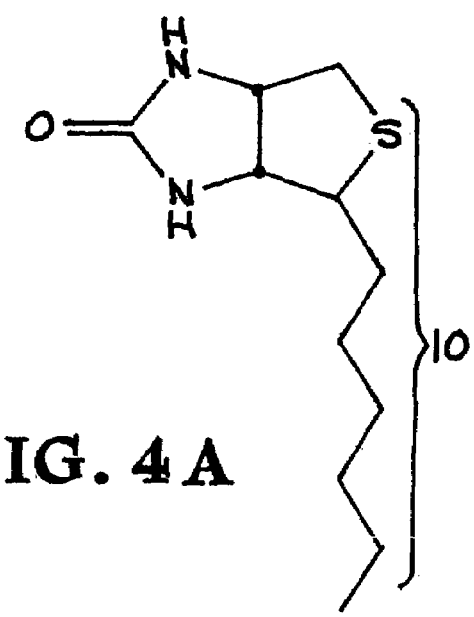
FIG. 4a shows the structure of the biotin functionalized anchor molecule attached to the pore walls of FIG. 4b.
Figure 4B:
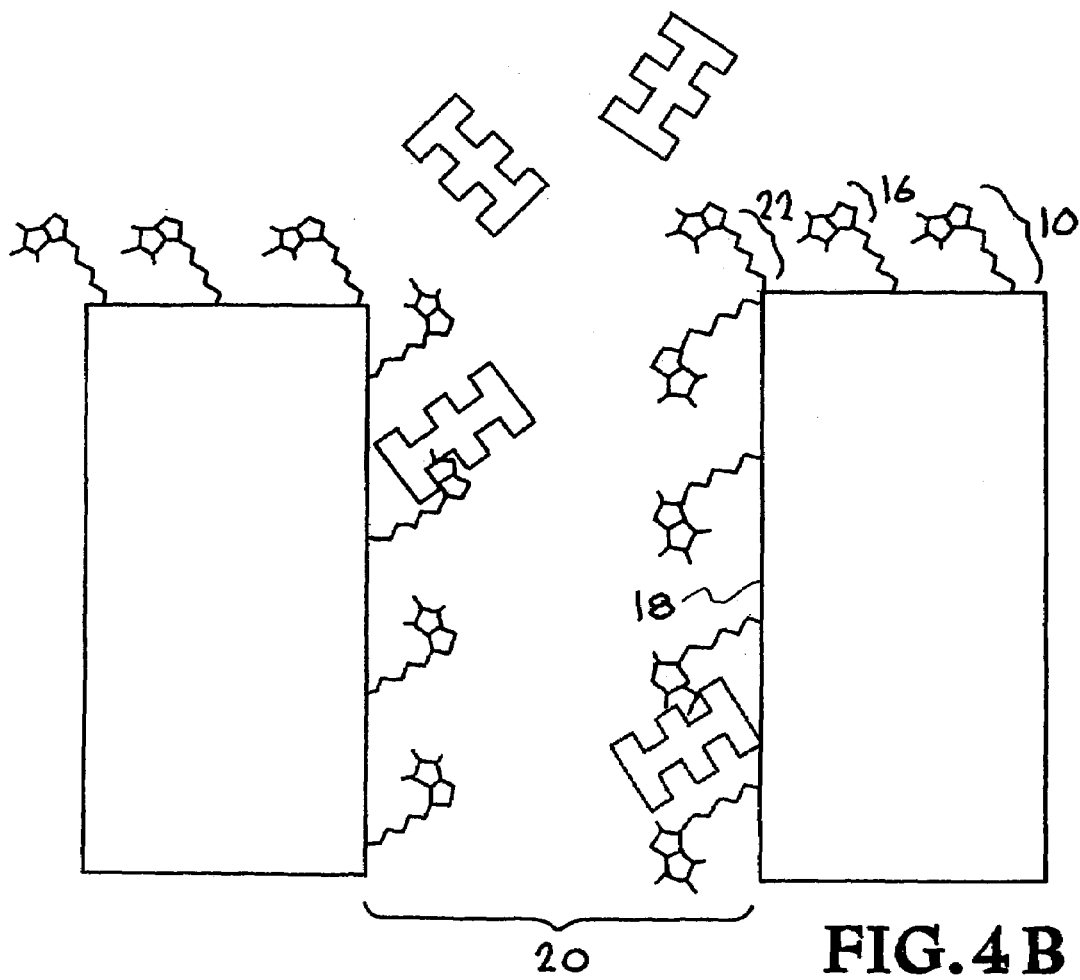
FIG. 4b is a schematic drawing of a pore functionalized with biotin exposed to streptavidin target molecules. (Not to scale)

Referring to FIGS. 3a, 3b, and 3c, membrane surfaces can be designed which selectively recognize and bind specific molecules. Chemical or biological anchors 10 typically comprise a functional group 12, a tether 14 (i.e., a carbon chain), and a receptor group 16 (e.g., an antibody, a single strand of DNA, a functionalized macro-cycle). Referring to FIG. 4b, these anchors 10 are immobilized on the pore walls 18 via covalent attachment of the tether. The structure of the anchor molecule attached the pore wall is shown in FIG. 4a. Chemical or biological selectivity is given by the receptor group on the anchor. The diameter of the pores 20, the length of the tether 22, and the nature of the receptor group 16 can be controlled and tailored to suit a variety of applications.

Surface chemistry can be used to filter out and/or detect specific chemical or biological target molecules. In addition, the binding of the target molecules to the anchors is not permanent. The receptor groups on the anchor can be treated to remove the target molecules and the filter reused. For example, a sulfur-sulfur bridge (S—S) can be introduced in the alkyl chain of the tether. Once the target is bound to the anchor and the experiment is finished, the S—S bridge can be reduced by addition of dithiothreitol (DTT) and the surface of the filter can be regenerated by reacting it with a new receptor group.

Fabrication and Functionalization

100 µm thick Si wafers are commercially available. Extra thinning can be achieved by mechanical or chemical polishing or by microfabrication techniques if necessary. A thin (ranging between a few hundred nanometers and a few hundred microns) silicon wafer, which is by definition a waveguide when standing in a low refractive index medium like air or water, can be converted into a photonic waveguiding filter by electrochemically etching pores through the wafer. A silicon membrane with an array of pores designed for waveguiding can be prepared using the techniques described in "Formation mechanism and properties of electrochemically etched trenches in n-type silicon," *J. Electrochem. Soc.* 137, 653–659 (1990) by Lehmann et al. For example, a triangular or hexagonal array of holes can be etched through a thin slab of silicon, wherein the light is guided in the device by total internal reflection. In the alternative, a line defect (e.g., like the one shown in FIG. 1a) can be introduced in the array of holes, wherein the light is then guided by the photonic crystal. This type of silicon membrane can be used to separate two phases.

Figure 5:
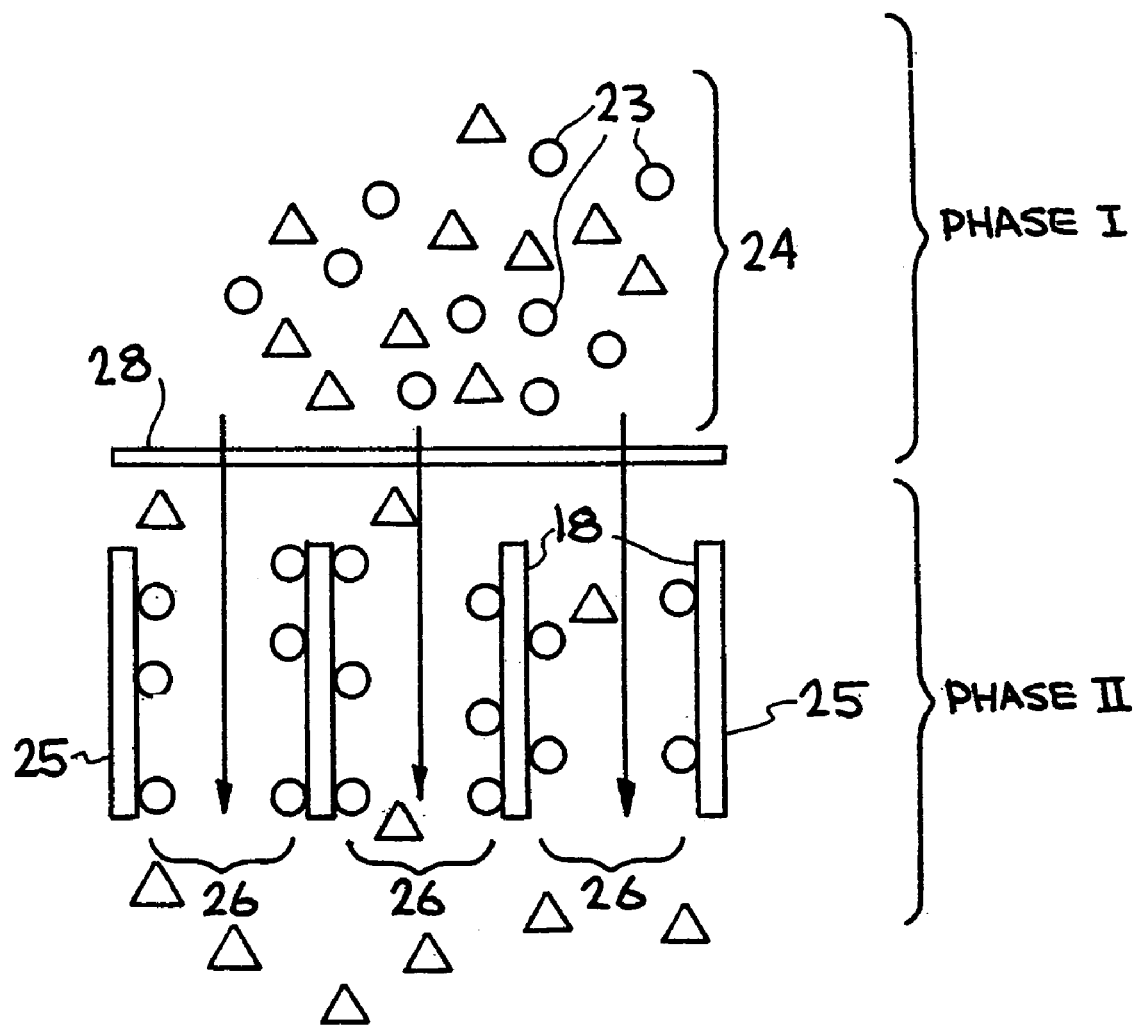
FIG. 5 shows a silicon membrane used to separate two phases.

Referring to FIG. 5, specific target molecules 23 can be removed from the first phase. Transport between the two phases through the membrane 25 can occur under the action of a driving force such as a concentration or a pressure difference.

After electrochemical formation in HF, the silicon pore walls 18 are passivated by hydrogen (they are covered by Si—H bonds). These Si—H bonds can be functionalized in two distinct ways. The first method employs ozone oxidation of the pore walls, which results in the generation of a hydroxylated silicon oxide surface, i.e., silanol bonds (Si—OH). The ozone oxidation is followed by condensation of the silanol groups with functionalized silanes, as described in Janshoff et al., "Macroporous p-type silicon Fabry-Perot layers. Fabrication, characterization, and applications in biosensing," *J. Am. Chem. Soc.* 120, 12108–12116 (1998). The second method employs hydrosilylation of alkenes or alkynes as described in Buriak et al., "Lewis acid mediated hydrosilylation on porous silicon," *J. Am. Chem. Soc.* 121, 11491–11502 (1999), followed by a reduction and subsequent reaction with functionalized groups such as esters. The properties of the resulting functionalized silicon pore surface, such as coverage, uniformity and stability, can then be characterized by a variety of techniques. Surface characterization measurements using atomic force microscopy (AFM), photoelectron spectroscopy (PES), soft X-ray fluorescence (SXF), X-ray absorption spectroscopy (XAS), Fourier Transform Infra Red Spectrometry (FTIR) and Mass Spectrometry (MALDI, MS) can be used to characterize the surface properties.

Under the first functionalization method, ozone oxidation of the pores generates a hydroxylated silicon oxide surface (silanol, Si—OH) which allows for subsequent condensation of the Si—OH groups along the pore walls with functionalized silanes. Some examples of functionalized silanes include $R'R_2Si(OCH_3)$ where $R=CH_3$ and $R'=$ a functional moiety such as, amine, thiol or modified ester. These functional groups can be reacted with cross linkers and then with biological or chemical anchors like antibodies and cyclodextrins. Cross linkers are carbon chains with functional groups designed to bind two molecules together, or to bind a molecule to a surface. Dancil et al. have designed porous Si biosensors that can detect antibody-antigen binding with this technique (see Dancil et al, "A Porous Silicon Optical Biosensor: Detection of Reversible Binding of IgG to a Protein A-Modified Surface," *J. Am. Chem. Soc.* 121, 11491–11502, 1999).

Under the second functionalization method, no oxidation is required. The hydride terminated silicon pore walls (Si—H) are reacted with alkenes or alkynes. This reaction leads to nitrile (—CN) terminated alkyl chains covalently attached on silicon via silicon-carbon bonds (Si—C). This reaction can be catalyzed by an aluminum based Lewis acid or thermally. The nitrile groups are then reduced to amine groups ($NH_2$) and the biological or chemical anchors are attached as described above in the first functionalization method.

Fabrication of Porous Silicon

Silicon Substrate

Step 1: Pre-patterning

Nucleation sites (inverted pyramids) are prepared on the surface of an n-type (phosphorus doped) silicon wafer by microfabrication (silicon nitride mask, photolithography and KOH etch). The silicon wafer is oriented orthogonal to the <100> crystallographic direction and the pores will grow along the <100> direction (orthogonal to the silicon wafer surface). The design of the mask corresponds to the geometry of the array: each inverted pyramid will correspond to a pore. There is no limitation on the design.

Step 2: Pore etching

The patterned substrate is mounted in a PVC electrochemical cell. The electrolyte is a mixture of hydrofluoric acid (HF), water and ethanol. The typical composition of the electrolyte solution is: 5% HF, 80% water and 15% ethanol by volume. Ethanol can also be replaced by a few drops of surfactant like Mirasol™ or Ilfotol™. The counter electrode is made out of platinum and is submerged in the electrolyte. The working electrode is contacted to the back of the substrate via indium gallium eutectic paste. The dissolution of silicon by HF requires the presence of positive charges. Since these charges cannot come from the doping in n-type silicon substrates, they are generated by back-side illumination. A tungsten halogen lamp is focused on the back of the sample and the infra-red (IR) wavelengths are removed with an IR filter. An ammeter measures the current photogenerated in the silicon wafer (photocurrent) and a constant voltage is applied between the two electrodes to induce an electric field attracting the positive charges on the nucleation sites (tip of the inverted pyramids). The pore length is proportional to the duration of the etch. The pore diameter increases with the photocurrent (the light intensity). Typical conditions to etch 500 nm diameter pores are: [HF]=5% by volume, 3 V applied and a photocurrent of 3 mA/cm$^2$.

Surface Activation (1) Ozone Oxidation:

Freshly etched silicon samples are exposed to ozone using an ozone generator for a few minutes. This provides an oxidized silanol (Si—OH) terminated surface. The samples are then refluxed overnight at room temperature in a 50 mM solution of functionalized methoxysilane in toluene.

After this first step, the samples are rinsed with toluene, ethanol, water and acetone and then dried under a stream of nitrogen. This procedure has been published by Janshoff et al. in "Marcroporous p-type silicon Fabry-Perot layers. Fabrication, characterization, and applications in biosensing," *J. Am. Chem. Soc.* 120, 12108–12116 (1998).

(2) Hydrosilylation:

Freshly etched silicon samples are placed in a round-bottom flask. The flask is evacuated, filled with nitrogen and sealed with a septum. A 1.0 M hexane solution of $EtAlCl_2$ is dropped onto the sample surface with a microliter syringe through the rubber septum, followed by an addition of the alkene (ex: pentene, dodecene) or alkyne (ex: pentyne, dodecyne), also via the septum. The sample is then left to react for 1–2H for the alkynes and for at least 12H for the alkenes. The sample is then quenched under inert atmosphere with THF, followed by $CH_2Cl_2$ and then removed to the ambient atmosphere. Finally, it is rinsed with ethanol and dried under a stream of nitrogen. This procedure has been published by Buriak et al. in "Lewis acid mediated hydrosilylation on porous silicon", *J. Am. Chem. Soc.* 121, 11491–11502 (1999). The same procedure can be done by thermal instead of chemical catalysis. In this case no $EtAlCl_2$ is added. Instead, the sample is covered with undecylenic acid and allowed to react at 95° C. for 16H. This procedure has been published by Boukherroub et al. in "Thermal hydrosilylation of undecylenic acid with porous silicon", *E.C.S.* 149, H59–63 (2002).

At the end of the surface activation (for both ozone oxidation and hydrosilylation) functional groups are attached to the silicon surface via a carbon chain (tether) covalently linked to the pore wall by a silicon-oxygen-silicon bond (Si—O—Si—R) or by a silicon-carbon bond (Si—C—R). Examples of functional groups are: amine (—NH$_2$), thiol (—SH) and esters like the standard maleimidobutyryloxydosuccinimide ester.

Functionalization of Porous Silicon

Once the functional groups described above are attached to the silicon pore walls, the immobilization of the chemical or biological anchors is done by standard cross linking chemistry. Examples of target molecule-anchor pairs include: any antigen-antibody pair, any single DNA-single DNA compliment pair, and any molecule, cell, bacteria or virus for which a specific anchor can be designed. Specific examples of anchors include the antibody biotin and the macro-cycle cyclodextrins. Many of these anchor molecules are commercially available with amine groups (—NH$_2$) ready to react with silicon surfaces that are activated with a modified ester such as, maleimidobutyryloxydosuccinimide ester.

Some specific examples of anchor-target molecule pairs follow: (1) the apolar lumen of cyclodextrins trap hydrophobic target molecules, (2) carbohydrates specifically bind to cell membrane proteins like lectins, (3) TWTCP(tetra-tryptophan ter-cyclo pentane) specifically binds to diphosphoril lipid which is present in the outer cellular membrane of gram-(-) bacteria, and (4) virus attachment on cells comprises the binding of a viral attachment protein to a cellular receptor, e.g., the haemagglutinin of Infuenza virus specifically binds to sialyoglycosaccharides and the glycoproteins of HIV bind to CD-4 proteins.

Immobilization of an amine functionalized anchor on a silicon surface activated with a modified ester can be done by incubating the silicon sample in a solution of the anchor molecule (1 mg/ml) in phosphate buffered saline (PBS) and DMSO for 30 min at room temperature. The sample is rinsed with DMSO, water and PBS. Similar procedures can be applied to the immobilization if the silicon surface is activated with an amine group. In that case, a modified ester functionalized anchor can be used.

Filter and Detection System

Figure 6:
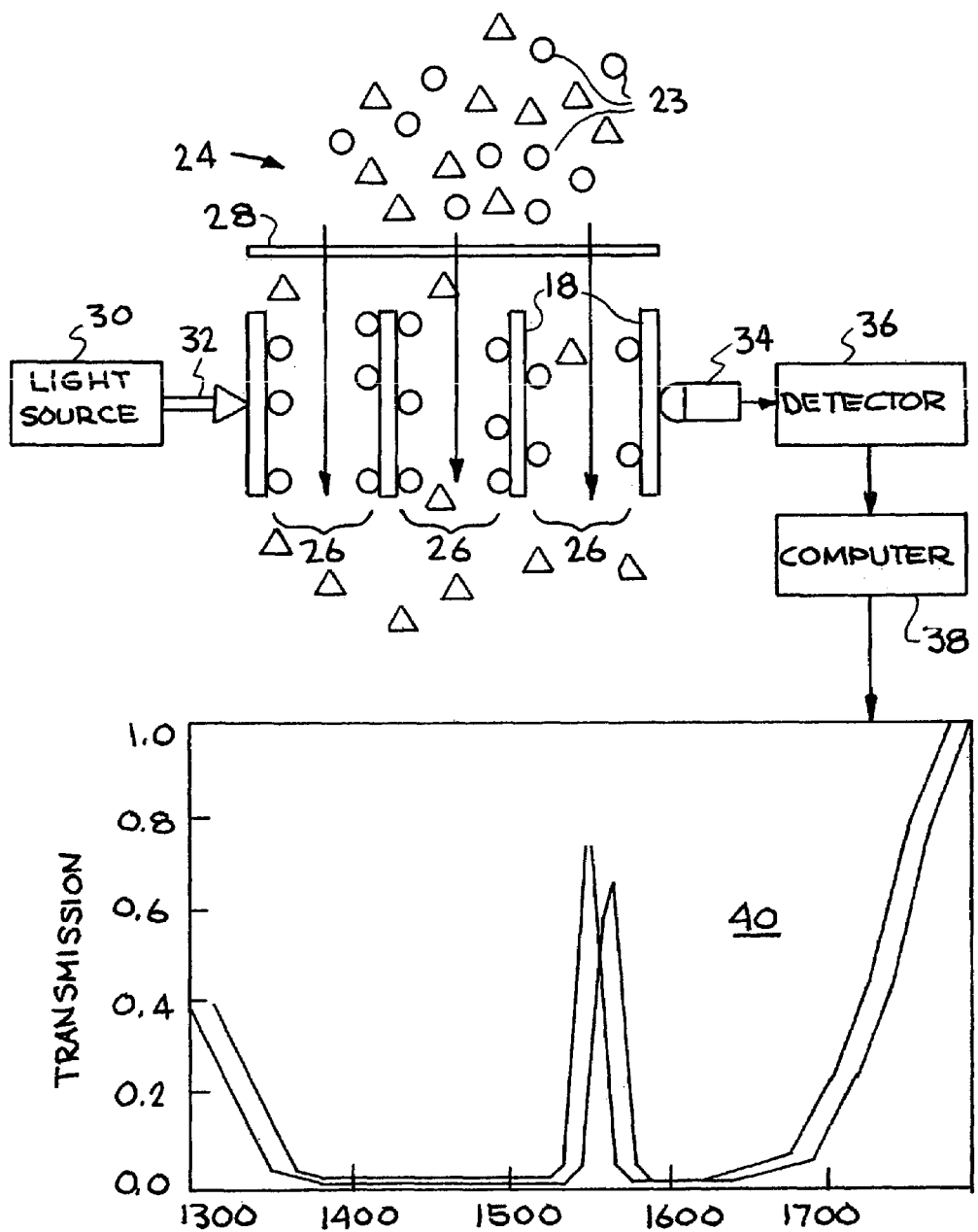
FIG. 6 is a schematic drawing of a photonic waveguiding filter system.

FIG. 6 shows a schematic a photonic waveguiding filter system in which a gas or liquid sample 24 to be analyzed runs parallel through a plurality of pores 26 having receptor-containing pore walls 18 in a photonic waveguiding silicon filter 28 while the transmission curve, i.e., the intensity of light transmitted through the device versus wavelength, is measured in real time. This system employs the end-fire coupling technique. Basically, light from a light source 30 is coupled into the device via a fiber optic 32 and a lens (not shown). An optical microscope (not shown) may be used to position the fiber optic on the waveguide. Light is then transmitted orthogonally to the pores through the photonic waveguiding silicon filter, detected by a microscope objective 34 and focused on a detector 36. Photomultiplier tubes or photodiodes are examples of effective detectors. A computer 38 converts the data to produce a graph 40 of the transmission curve, i.e., the intensity of the light transmitted through the photonic filter versus the wavelength. It detects the presence of a target 23 bound in the device and calculates its concentration.

The silicon waveguiding collection and detection filter allows measurements in situ and in real time. The filter can be used to monitor air pollution, water contamination, and to detect the presence of specific chemical or biological molecules in gas or liquid samples. The filter can be made to have dimensions less than 200 μm×1 cm×1 cm. The full device, with the optics, can be engineered to fit in one hand and a laptop computer can be attached to the system to read the target concentration data.

Binding of target molecules on the receptor-containing pore walls is detected by a shift of the transmission curve of the waveguiding filter due to an increase of the dielectric constant of the pores. In this configuration, as the gas or liquid to be analyzed runs through the pores, target molecules will bind to the anchors that have been attached to the pore walls. The device will operate with or without the introduction of defects in the waveguide. However, the introduction of defects in the waveguide can dramatically increase the sensitivity of the device because a small shift of position of a sharp spectral feature induces a large intensity difference at a given wavelength. Referring to FIG. 6, graph 40 illustrates that, if following a sharp mode in the band gap (defect), a small spectral shift can induce a large intensity shift at a given wavelength.

The sensitivity of the device is maximized by calculating the optimal pore size and pore spacing along with the position of the defects, i.e., missing pores. The transfer-matrix technique for the propagation of EM waves in dielectric structures described by Sigalas et al in, "Photonic band gaps and defects in two dimensions; studies of the transmission coefficient", *Phys. Rev.* B48, 14121–14126 (1993), can be adapted to perform the calculations. The system studied by Sigalas et al. consists of silicon rods in air and the present system consists of air rods in silicon, so a change of the dielectric constants entered in the program is required. The transfer-matrix technique takes into account dispersion, i.e., the variation of the dielectric constant with the wavelength, and absorption. It also allows the introduction of multiple defects in the periodic structure of the photonic crystal.

The transmission curves of the photonic filters are calculated when the device is in air (for gas phase applications) or buffer (for liquid phase applications) and has no target molecules bound to it. The same calculations are then performed after target molecules bind. The spectral shift of the band edge and/or of the defect states in the band gap due to the binding of the target molecules can be extracted for various device configurations (pore size, pore spacing, defect nature and position). The optimal configuration can be deduced theoretically and then built and tested. Pores having diameters ranging in size from about 100 nanometers to about 1 micron are effective and can be fabricated by the process outlined above. The pore diameter should be adapted to the target. For example, detection of large biological targets such as bacteria require pores in the micron range. Viruses and large proteins require pores in the 100 nm range. Small proteins and chemical compounds require pores in the 50 nm range. The higher the change of refractive index of the pore upon binding, the higher the shift in the transmission curve and the lower the detection level. The refractive index change scales with the filling fraction of the pore by the target. Therefore, a pore size adjusted to the target size will increase the filling fraction for low concentrations and the refractive index change will be optimized. It is also important to note that a modification of pore diameter induces a spectral shift of the band gap. The wavelength of light shone through the device will then have to be adjusted to probe the relevant spectral region. For example, micron sized pores lead to band gaps in the IR range and 100 nm sized pores lead to band gaps in the visible range.

EXPERIMENTAL METHODS

Membrane Pre-Patterning

N-type, phosphorus-doped, (100)-oriented silicon wafers with a resistivity of 2 Ωcm and an initial thickness of 545 μm (Silicon Quest International, Santa Clara, Calif.) were pre-patterned on both sides by standard contact photolithography. A thin layer of silicon nitride (0.2 μm) was grown on the surface of the silicon wafers by low-pressure chemical vapor deposition, and the top and bottom patterns were defined by plasma etch. The top pattern consists of 2×2 μm squares fully etched with potassium hydroxide (KOH; Mallinckdrodt) to form pyramid-shaped pits. These pits are arranged into a square lattice with a 4 μm period. They constitute nucleation sites for the growth of the membrane pores. The bottom pattern consists of 250×250 μm square windows etched in KOH to reduce the thickness of the silicon wafer from 545 μm to 45 or 15 μm. Each sample is a 1×1 cm square, entirely patterned with pyramidal pits on the top and patterned with 25 back windows.

Membrane Etching

Silicon membranes were prepared by backside, light-assisted electrochemical etch of pre-patterned silicon samples. The samples were mounted in an electrochemical cell and connected to a potentiostat (Princeton Applied Research, model 273A). An ampere meter (Hewlett-Packard, model 3466A) was introduced in the circuit to measure the photocurrent. The electrolyte solution was a mixture of deionized water (97.5% per volume) and HF (Aldrich; 2.5% by volume). A drop of surfactant (Ilfotol, Ilford, UK) was added to 250 ml of prepared solution. The counter electrode was a platinum coil immersed in the electrolyte, and the work electrode was connected to the sample by gallium-indium eutectic paste (Aldrich), which provides an ohmic contact. The positive charges required for the dissolution of silicon in the presence of HF were created on the back of the sample by the white light from a tungsten lamp. The light was filtered with a BG-12 filter, transmitting wavelengths between 250 and 500 nm to stop deep-penetrating infrared light. The light intensity was varied to generate a photocurrent between 200 and 500 pA per pore. A 1.5 V bias was applied across the sample to generate an electric field that localizes the electrochemical dissolution reaction at the tip of the nucleation pits.

For the functionalized membranes, the silicon nitride top and bottom masks were kept on the samples to prevent derivatization, and consequently, to reduce binding of the microbeads on the top and bottom surface. Contact was made on the back of the sample by removing the nitride on a small area and rubbing on some of the gallium-indium eutectic paste. The nitride covering the top area exposed to the electrolyte solution during the membrane fabrication was removed before starting the electrochemical reaction, by a 30 min exposure to an aqueous solution of HF (25% by volume) in the electrochemical cell.

Membrane Functionalization

The hydride-terminated silicon membranes were functionalized with biotin using a five-step procedure as described in Hart et al. "New Method for Attachment of Biomolecules to Porous Silicon," *Chem. Comm.* 3, 322–323, 2003. The procedure includes hydrosilylation, reduction of the surface bound nitrile, attachment of SPDP (N-succinimidyl 3-(2-pyridyldithio) propionate; Aldrich), reductive cleavage of pyridyl disulphide protecting group, and finally, attachment of biotin (Aldrich). Hydrosilylation of the silicon membranes was carried out in a roundbottom Schlenk type flask equipped with a single 24/40 taper joint and glass stopcock controlled side-arm. The samples were placed in the flask which was then sealed with a septum and purged with dry, oxygen-free nitrogen gas. 5-Hexynenitrile (0.10 mL, 0.95 mM) was added to the samples followed by the addition of a 1.0 M hexane solution of $EtAlCl_2$ (150 μL, 0.15 mM). After 3 h at room temperature, the membranes were washed under a nitrogen atmosphere with THF, followed by $CH_2Cl_2$ and then EtOH. They were then dried under vacuum. Reduction of the surface bound nitrile to a 1° amine was achieved by adding a 1.0 M diethyl ether solution of $LiAlH_4$ (150 μL, 0.15 mM). After 30 min at room temperature, the membranes were washed under a nitrogen atmosphere with THF (3×5 mL), followed by $CH_2Cl_2$ (3×5 mL) then EtOH (×5 mL) then dried under a nitrogen stream followed by vacuum. The amino functionalized membranes were immersed in a solution of SPDP (2 mg, $6.4 \times 10^{-3}$ mM) in DMF under nitrogen and left to react for 3 h with occasional agitation. The remaining SPDP solution was removed and the samples were rinsed with DMF (3×5 mL) followed by ethanol (3×5 mL) then dried under a nitrogen stream followed by vacuum. The SPDP functionalized membranes were immersed in a solution of dithiothreitol (DTT) (15.4 mg, 0.1 mM) in 10% EtOH/H2O (10 mL) and left to react for 1 h with occasional agitation. The remaining DTT solution was removed and the parts were rinsed with fresh 10% EtOH/H2O (3×5 mL) then EtOH (5×5 mL) then dried under a nitrogen stream followed by vacuum. The sulfhydryl samples were immersed in a solution of GMBS (N-(γ-maleimidobutyryloxy)succinimide)) (2.0 mg, $7.1 \times 10^{-3}$ mM) in DMF under nitrogen and left to react for 3 h with occasional agitation. The remaining GMBS solution was removed and the samples were rinsed with DMF (3×5 mL) followed by ethanol (3×5 mL) then dried under a nitrogen stream followed by vacuum. The NHS-ester membranes were immersed in a solution of Biotin cadaverine (5.0 mg, 0.011 mM) in DMF under nitrogen and left to react overnight with occasional agitation. The remaining solution was removed and the samples were rinsed with DMF (5×5 mL) followed by ethanol (5×5 mL) then dried under a nitrogen stream followed by vacuum.

Membrane Characterization

The samples were characterized by field-emission scanning electron microscopy with an Hitachi S-4500 microscope. Samples were mounted on the sample holder using carbon tape and graphite paint. SEM images were taken with an acceleration voltage between 3 and 6 KeV. Both back-scattered and secondary electron images were acquired.

Membrane Permeation

Uncoated polystyrene dyed beads with diameters ranging from 0.04 to 4.0 μm and streptavidin-coated polystyrene dyed beads with a diameter of 0.2 μm were purchased from Bangs Laboratories, Fishers, Ind. For the membrane permeation experiments, bead solutions containing $10^7$ beads $ml^{-1}$ and 0.001% of the surfactant Triton X (Sigma) in de-ionized water were prepared. Triton X was added for wetting purposes. Each membrane was mounted into a U-tube diffusion chamber, with feed solution on one side and atmospheric pressure on the other side. A sealed piston was used to push 5 ml of feed solution through the membrane at a flow rate of 0.5 ml $cm^{-2}$ $min^{-1}$. Alternatively, the membranes were sealed with aluminium tape and Parafilm on a metallic support grid, and inserted into the stainless steel filter holder of a Luer syringe with Teflon O-rings. The fluorescence of the feed and permeate solutions was measured with a Perkin Elmer fluorimeter model LS45 to assess the bead concentration in each solution. After each of the experiments, 5 ml of deionized water were pushed through the membrane at a speed of 0.5 ml cm$^{-2}$ min$^{-1}$ to flush adsorbed beads out of the pores. The fluorescence data from the permeate solution were corrected from this dilution by a factor of two.

Physical and Optical Properties of Dyed Polystyrene Micro-Beads Used

Figure 7A:
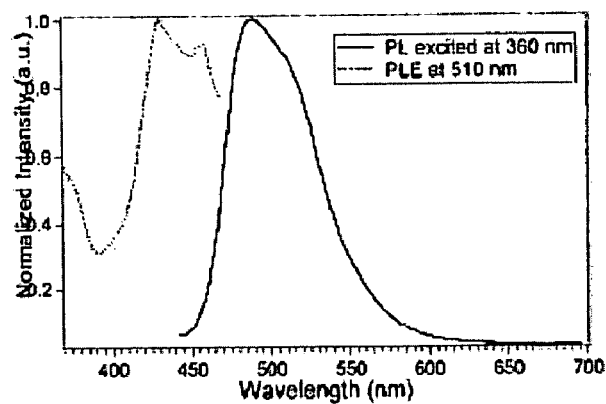
FIG. 7a shows the photoluminescence excitation spectrum at 510 nm and 360 nm.
Figure 7B:
FIG. 7b is an SEM picture of the smallest beads used.
Figure 8A:
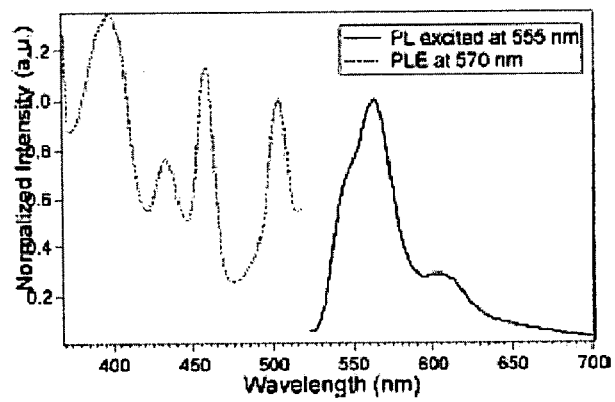
FIG. 8a shows the photoluminescence excitation spectrum 570 nm and 555 nm.
Figure 8B:
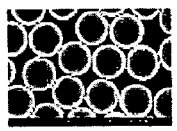
FIG. 8b is an SEM picture of the largest beads used.

FIG. 7a shows the photoluminescence excitation spectrum at 510 nm and the photoluminescence excited at 360 nm. An SEM picture of the smallest beads used having a diameter of 0.04 µm is shown in FIG. 7b. FIG. 8a shows the photoluminescence excitation spectrum at 570 nm and the photoluminescence excited at 555 nm. An SEM picture of the largest beads used having a diameter of 4 µm is shown in FIG. 8b.

Permeation of Silicon Membranes by Dyed Polystyrene Microbeads

Figure 9:
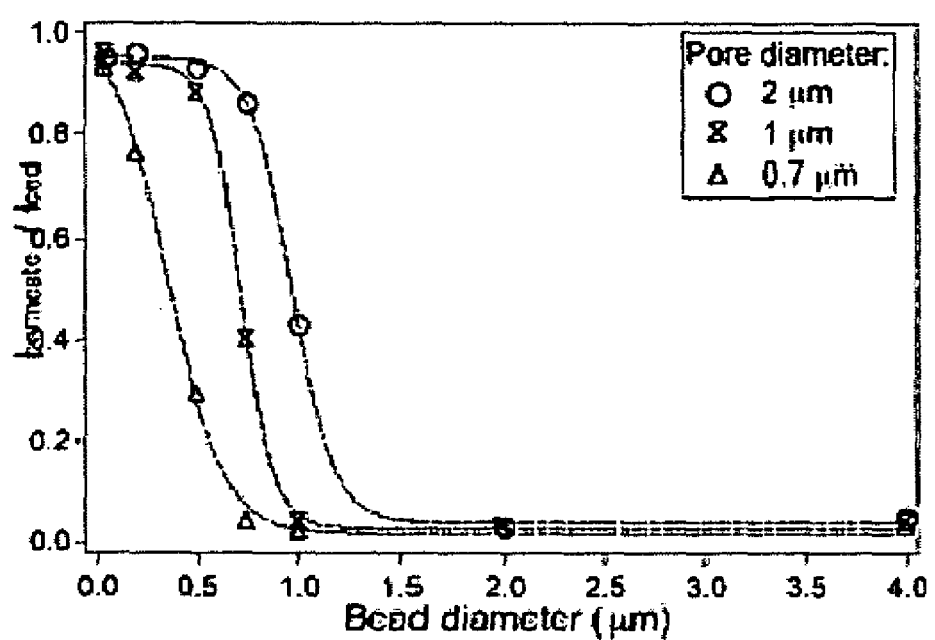
FIG. 9 shows size exclusion curves for three membranes with varying pore diameters.

The size exclusion properties of the silicon membranes as well as the absence of holes and cracks were tested by flowing size calibrated micro-beads through the devices and by measuring the ratio of the photoluminescence of the feed to the permeate solutions. Each device was tested with 7 solutions containing beads with diameters ranging from 0.04 µm to 4 µm in order to build the size exclusion curve. FIG. 9 shows size exclusion curves for three membranes with pore diameters ranging from 0.7 µm to 2 µm.

EXPERIMENTAL RESULTS

Disclosed herein are the first functionalized silicon membranes. Also disclosed is their ability to selectively capture simulated bio-organisms. These extremely versatile and rigid devices are able to recognize the external fingerprints of bio-organisms—such as size and outer membrane proteins—for specific capture and detection applications. Pores were etched on pre-patterned silicon substrates, their walls were functionalized with antibodies (covalently attached), and the ability of the functionalized membranes to capture simulated bio-organisms was tested.

Figure 10A:
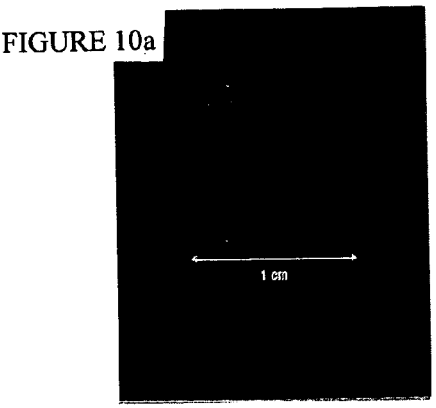
FIGS. 10a–10d are pictures of a pre-patterned silicon sample.
Figure 10B:
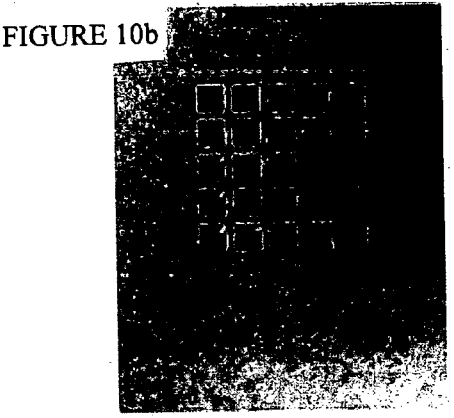
Figure 10C:
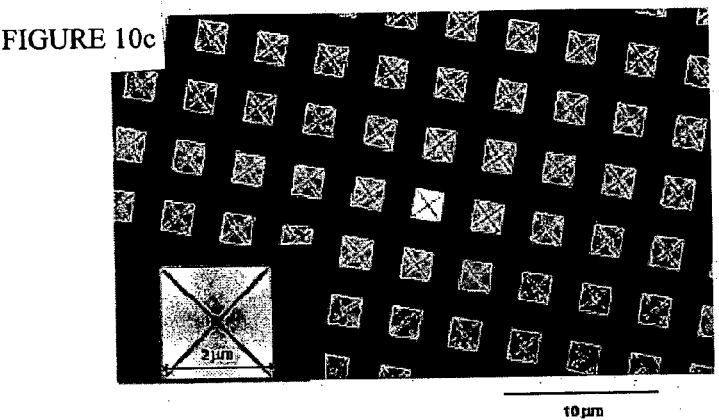
Figure 10D:
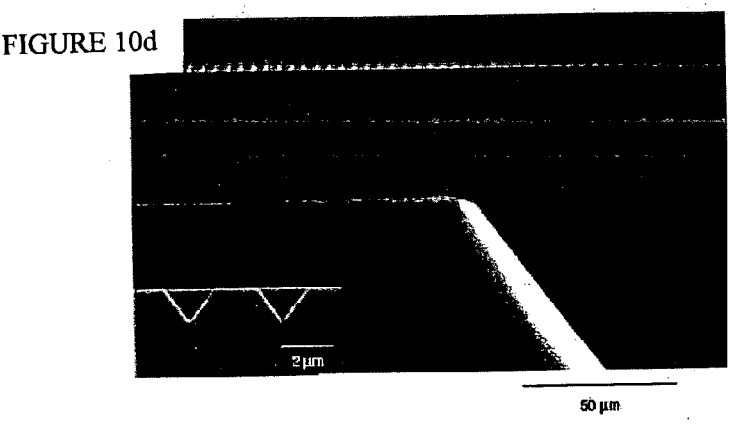

Through pores were prepared on pre-patterned n-type silicon wafers using the backside illumination technique described by V. Lehmann and H. Foll in "Formation Mechanism and Properties of Electrochemically Etched Trenches in N-Type Silicon." *J. Electrochem. Soc.* 137, 653–659 (1990). In this method, the top of the wafer is patterned with inverted pyramid-shaped pits by standard lithography. The purpose of these top pits is to concentrate the electric field and to constitute nucleation sites for the pore growth as shown in FIGS. 10a and 10c. FIG. 10 shows a pre-patterned silicon sample: FIG. 10a shows an optical top view; FIG. 10b shows an optical bottom view; FIG. 10c shows a scanning electron microscope (SEM) top view and insert with detail of one pyramidal pit; and FIG. 10d shows an SEM cross-section and insert with detail of two pyramidal pits. A back pattern was added that provides high robustness to the devices and allows membrane thickness tunability. Twenty-five back windows were prepared by lithography, followed by potassium hydroxide (KOH) directional etch to define 25 membrane areas per sample as shown in FIG. 10b. The initial wafer thickness of 545 µm was thinned down to 45 µm under the back windows as shown in FIG. 10d. The thickness of the silicon slab remaining under the back windows defines the membrane thickness, and is controlled by the KOH etch time. The advantage of this design is that it combines thin silicon membrane areas with a thick silicon support grid. None of the membranes etched on back-patterned wafers cracked or broke during the experiments.

Figure 11A:
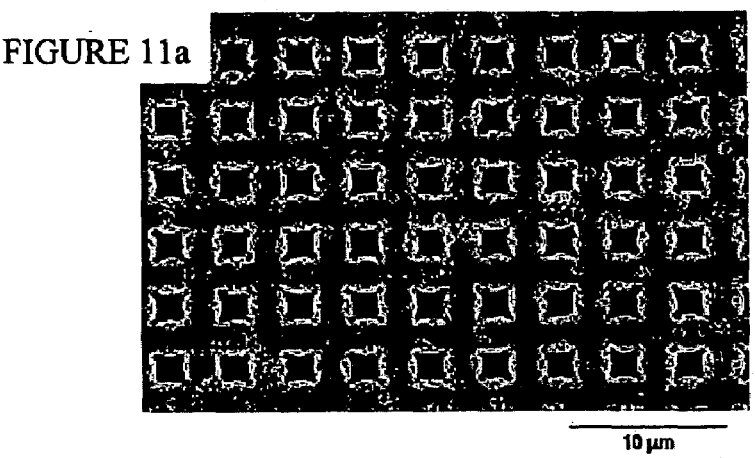
FIGS. 11a–11d are SEM pictures of a silicon membrane with a thickness of 15 µm and a pore diameter of 2 µm.
Figure 11B:
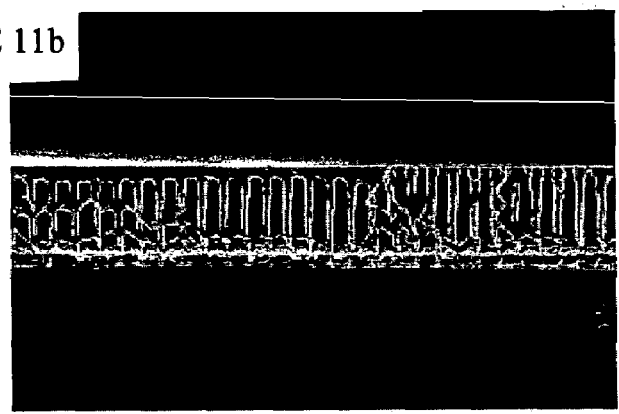
Figure 11C:
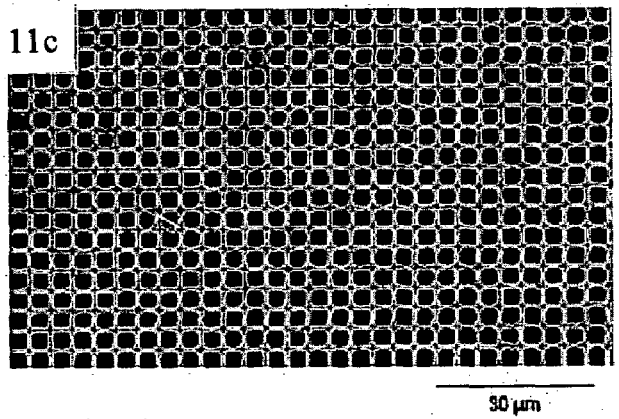
Figure 11D:
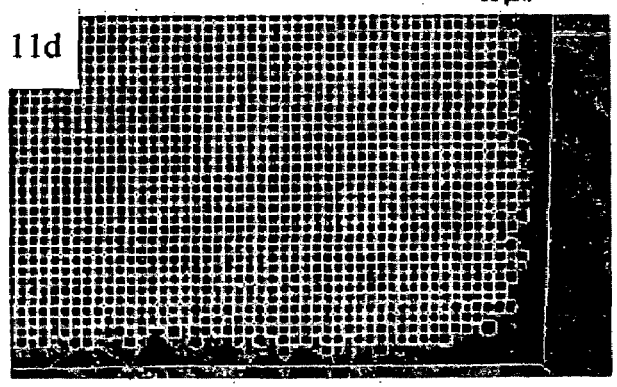
Figure 12A:
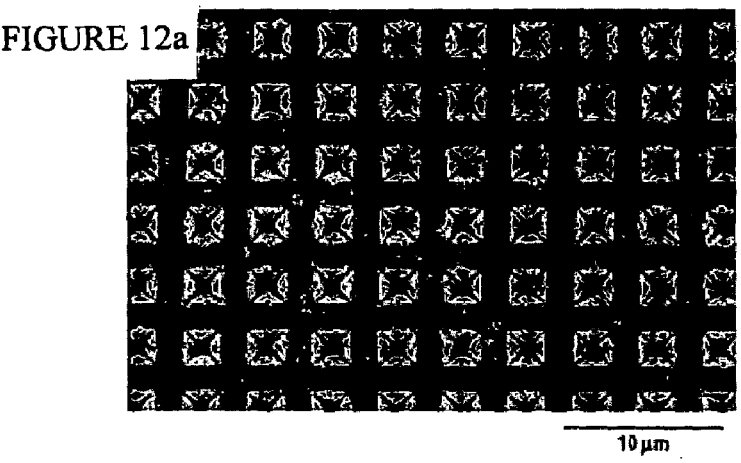
FIGS. 12a–12d are SEM pictures of a silicon membrane with a thickness of 45 µm and a pore diameter of 0.5 µm.
Figure 12B:
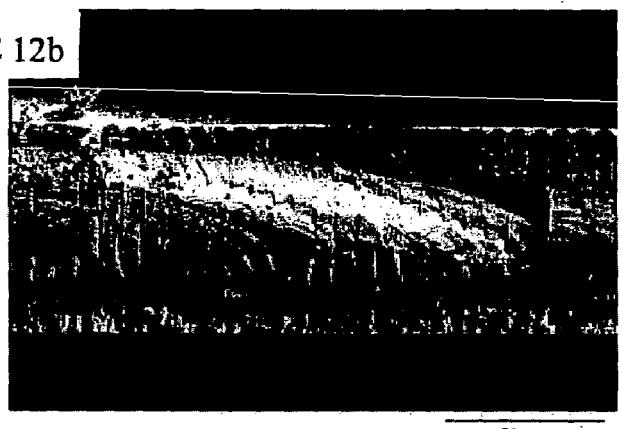
Figure 12C:
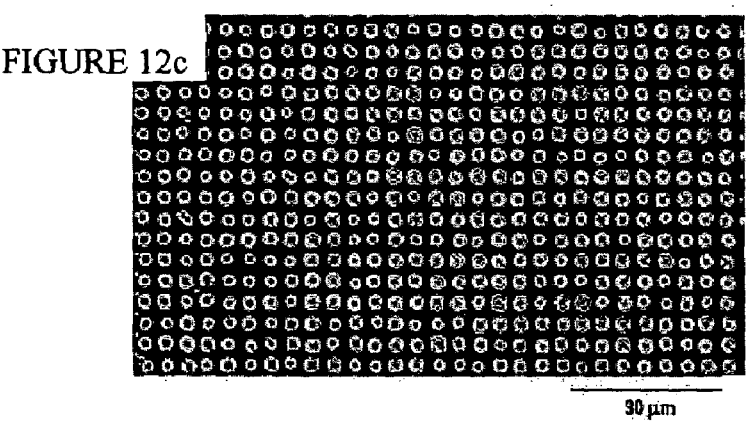
Figure 12D:
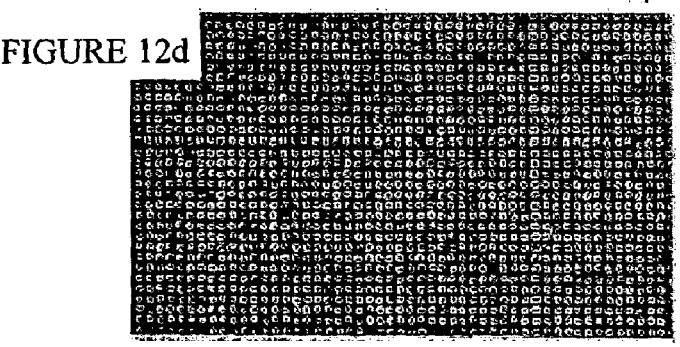

The pre-patterned samples were etched in an electrochemical cell in an aqueous solution of hydrofluoric acid (HF). The positive charges required to dissolve silicon in this electrolyte were photo-generated on the back of the n-type wafer, and concentrated at the tips of the top nucleation pits by applying a voltage across the sample as described in the Experimental Methods discussion above. The pore diameter was tuned by controlling the number of positive charges collected at the pit tips, which depends on the intensity of the back illumination. The pore length is proportional to the duration of the HF etch. Although the entire top surfaces of the samples were patterned with nucleation sites, pores grew only in the thinned areas, where the electric field is the most intense. The pore growth rate was measured to be 0.25±0.05 µm min$^{-1}$. Etching pre-patterned wafers thinned down to 15 µm for one hour led to the formation of through pores in the back windows, as shown in FIG. 11b. FIGS. 11a–11d show SEM pictures of a silicon membrane with a thickness of 15 µm and a pore diameter of 2 µm. FIGS. 12a–12d show SEM pictures of a silicon membrane with a thickness of 45 µm and a pore diameter of 0.5 µm. As seen in FIGS. 11 and 12, the pore diameter enlarges toward the end of the etch (the bottom of the pore) due to an increased number of positive charges at the back of the sample. With this etching technique, the membrane pore diameter was tuned between 0.5 and 2.0 µm by increasing the light intensity to generate a photocurrent between 200 and 500 pA per pore. The absence of holes and cracks in the membranes, as well as their size-exclusion ability, were checked by mounting the devices in a U-tube permeation cell fitted with a sealed piston, and by measuring the fluorescence of feed and permeate solutions of size-calibrated dyed microbeads forced through the pores. Seven aqueous solutions containing beads with diameters ranging between 0.04 and 4.0 µm were used. A good correlation between the membrane cut-off determined by the bead solution assay and the pore diameter measured by scanning electron microscopy (SEM) was observed, indicating sharp pore-size distributions. The Lewis acid catalyzed reaction was chosen because it has been demonstrated by J. Buriak and M. Allen in "Lewis Acid Mediated Functionalization of Porous Silicon with Substituted Alkenes and Alkynes," *J. Am. Chem. Soc.* 120, 1339–1340 (1998), to stabilize porous silicon samples in very demanding conditions, such as boiling in aerated water or in aqueous KOH at pH=10, as well as in simulated human blood plasma. (See Canham, L. T. et al. "Derivatized Mesoporous Silicon with Dramatically Improved Stability in Simulated Human Blood Plasma," *Adv. Mater.* 11, 1505–1507, 1999.) This technique can be used to anchor biotin on porous silicon surfaces by an extension of the linker. (See Hart, B. R. et al. "New Method for Attachment of Biomolecules to Porous Silicon," *Chem. Comm.* 3, 322–323, 2003.) The procedure used for biotin is general to the covalent attachment of any kind of biomolecule (for example, any accessible lysine site can be attached to the linker). This reaction also works on flat silicon surfaces. Flat silicon surfaces were functionalized with biotin and incubated in a solution of streptavidin-coated microbeads for 45 min. After rinsing extensively with deionized water, about 40% of the area of the functionalized samples was coated with a monolayer of microbeads; no beads were found on unfunctionalized reference surfaces.

Figure 13:
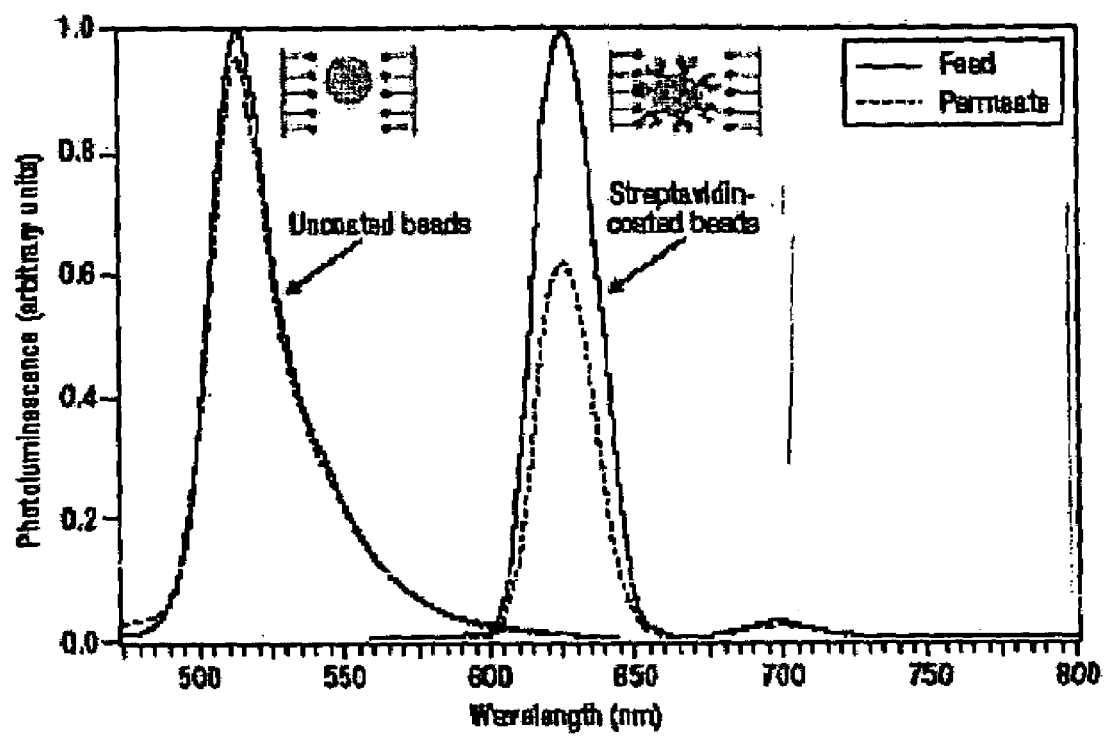
FIG. 13 is a photoluminescence spectrum showing selective capture of simulated bio-organisms.
Figure 14:
FIG. 14 is an SEM cross-section of streptavidin beads captured in a biotin-functionalized pore.

Because of the large bead size, the surface coverage estimated with the beads is higher than the 20–30% surface coverage reported by J. Buriak in "Organometallic chemistry on silicon and germanium surfaces," *Chem. Rev.* 102, 1271–1308, 2002, for Lewis acid catalyzed attachments on porous silicon. The same functionalization on the silicon membranes was performed (see Experimental Methods). Wetting problems when starting the functionalization on pores covered with hydrophobic silicon hydride were avoided because none of the reaction steps involves aqueous solutions. FIG. 13 shows the result of a flow-through experiment performed on a biotin-functionalized silicon membrane with a pore diameter of 2.0 µm, and 200 nm diameter beads. Luminsescence of feed and permeate solutions of uncoated (left) and atreptavidin-coated (right) microbeads pushed through a biotin-functionalized silicon membrane with a pore diameter of 2 µm and a thickness of 45 µm. Both kinds of beads have a 200 nm diameter. The uncoated beads were dyed with a green dye and the streptavidin-coated beads were dyed with an orange dye. When the uncoated beads were pushed through the membrane, the fluorescence of the permeate solution was identical to the fluorescence of the feed solution, showing that no beads were captured in the pores. When streptavidin-coated beads of the same diameter were pushed through the membrane at the same speed, the fluorescence signal of the permeate solution decreased by 40±4% (results from experiments performed on three identical devices). FIG. 14 shows an SEM cross-section of streptavidin-coated microbeads captured and anchored on the walls of a biotin-functionalized pore. The number of beads captured in the membrane pores can be extracted from the concentrations of the feed and permeate solutions (corrected from the deionized water flow-through rinses) and divided by the number of pores. The average number of beads captured per pore was found to be about 42±4 beads per pore. This number is well correlated with the number of beads trapped per pore, 38±10, counted by SEM on cross-sections of the functionalized membranes performed after the flow-through experiments. The deficit of beads observed by SEM is due to beads attached on the top surface of the sample. Almost no beads where observed on the bottom surface of the sample because the silicon nitride mask was kept on the support grid to prevent biotin functionalization, and because the interaction time between the liquid and the bottom surface is short. It is not possible to keep the top silicon nitride mask on because silicon nitride dissolves during the HF electrochemical etch.

The 40% trapping efficiency obtained for a pore-to-bead diameter ratio of 10 can be optimized by adjusting the physical parameters of the membrane, such as the pore diameter, length and density, according to the requirements of specific applications. For example, a decrease of the pore-to-organism diameter ratio will improve the capture rate at low organism concentration, but increase the probability of pore clogging at high organism concentration. A report by S. Lee et al. titled "Antibody-based Bio-nanotube Membranes for Enantiomeric Drug Separation" in *Science* 296, 2198–2200 (2000), on a transport selectivity coefficient of 2.6 for an enantioselective bionanotube membrane (the selectivity coefficient being the ratio of the fluxes of the RS to the SR enantiomers of the drug 4-[3-(4-fluorophenyl)-2-hydroxy-1-[1,2,4]triazol-1-yl-propyl]-benz permeating through the device) places the trapping efficiency obtained into perspective. This selectivity coefficient, obtained for a pore diameter of 0.035 µm, was increased to 4.5 by reducing the pore diameter to 0.020 µm, but at the price of a significant analyte flux reduction. Selective capture of bioorganisms such as bacteria and viruses, which have a size comparable to the size of the microbeads used in the present work, and which differ from one another by specific outer membrane proteins, simulated by the streptavidin anchored on the bead surface are expected to work equally well.

The disclosures of the publications, patents, and published patent specifications referenced in this application are hereby incorporated by reference into the present disclosure to more fully describe the state of the art to which this invention pertains.

All numbers expressing quantities of ingredients, constituents, reaction conditions, and so forth used in the specification and claims are to be understood as being modified in all instances by the term "about". Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

While various materials, parameters, operational sequences, etc. have been described to exemplify and teach the principles of this invention, such are not intended to be limited. Modifications and changes may become apparent to those skilled in the art; and it is intended that the invention be limited only by the scope of the appended claims.

The invention claimed is:

1. A photonic waveguiding device comprising:
    at least one silicon wafer having a plurality of through pores, wherein said pores are distributed according to a designed pattern leading to a photonic band gap; and
    at least one chemical or biological target specific anchor attached to the inner wall of at least one of said pores, wherein said anchor is attached to said pore wall via silicon-carbon covalent bonding.

2. The photonic waveguiding device recited in claim 1, wherein said pores have pore diameters ranging in size from about 100 nm to about 1 µm.

3. The photonic waveguiding device recited in claim 1, wherein the total size of said device has dimensions no larger than 200 µm×1 cm×1 cm.

* * * * *